US009907521B2

(12) United States Patent
Papaix et al.

(10) Patent No.: US 9,907,521 B2
(45) Date of Patent: Mar. 6, 2018

(54) RADIATION SENSOR WITH X-RAY DETECTION

(71) Applicant: Teledyne e2v Semiconductors SAS, Saint-Egrève (FR)

(72) Inventors: Caroline Papaix, Quaix-en-Chartreuse (FR); Florian Julien, Mid Levels (HK); Nathalie Pascal, Le Sappey-en-Chartreuse (FR); Stéphane Crespin, Vourey (FR)

(73) Assignee: TELEDYNE E2V SEMICONDUCTOR SAS, Saint Egreve (FR)

( * ) Notice: Subject to any disclaimer, the term of this patent is extended or adjusted under 35 U.S.C. 154(b) by 0 days.

(21) Appl. No.: 15/547,095

(22) PCT Filed: Jan. 15, 2016

(86) PCT No.: PCT/EP2016/050730
§ 371 (c)(1),
(2) Date: Jul. 28, 2017

(87) PCT Pub. No.: WO2016/120091
PCT Pub. Date: Aug. 4, 2016

(65) Prior Publication Data
US 2018/0008214 A1    Jan. 11, 2018

(30) Foreign Application Priority Data
Jan. 30, 2015 (FR) ...................................... 15 50738

(51) Int. Cl.
A61B 6/14      (2006.01)
A61B 6/00      (2006.01)
(Continued)

(52) U.S. Cl.
CPC ............ A61B 6/145 (2013.01); A61B 5/0088 (2013.01); A61B 6/4233 (2013.01);
(Continued)

(58) Field of Classification Search
CPC ..... G01T 1/2018; A61B 6/145; A61B 6/4233; A61B 6/545; A61B 6/5205; A61B 6/14; A61B 6/54; H01N 5/32
(Continued)

(56) References Cited

U.S. PATENT DOCUMENTS

| 5,510,623 A | 4/1996 | Sayag et al. |
| 2006/0193436 A1 | 8/2006 | Schick et al. |

(Continued)

FOREIGN PATENT DOCUMENTS

| EP | 0757474 A1 | 2/1997 |
| FR | 2930841 A1 | 11/2009 |

(Continued)

OTHER PUBLICATIONS

International Search Report and Written Opinion for PCT/EP2016/050730, dated Apr. 20, 2016.

*Primary Examiner* — David Porta
*Assistant Examiner* — Faye Boosalis
(74) *Attorney, Agent, or Firm* — Hauptman Ham, LLP; Sean A. Passino

(57) ABSTRACT

The invention relates to medical imaging and, more specifically, to intraoral dental radiology. The sensor according to the invention includes a series (SPHx) of detection photodiodes for detecting the arrival of an X-ray flash. The series of photodiodes occupies the location of a central column of the matrix of pixels. The signal of the missing pixel in each row can be reconstructed by interpolating the signals provided by the adjacent pixels of the row. The detection photodiodes are identical to the photodiodes of the active (Continued)

CMOS pixels. They are all electrically connected on one side to a reference potential and on the other side to a detection conductor (CD) extending along the series of photodiodes. This detection conductor is connected to a detection circuit (DX) delivering a signal for triggering the capture of an image when the detected current or the variation in this current exceeds a threshold showing that an X-ray flash has been initiated.

7 Claims, 3 Drawing Sheets

(51) Int. Cl.
 H04N 3/14 (2006.01)
 A61B 5/00 (2006.01)
 G01T 1/20 (2006.01)

(52) U.S. Cl.
 CPC ............ *A61B 6/5205* (2013.01); *A61B 6/545* (2013.01); *G01T 1/2018* (2013.01); *H04N 3/155* (2013.01)

(58) Field of Classification Search
 USPC .......................................................... 378/98.8
 See application file for complete search history.

(56) References Cited

U.S. PATENT DOCUMENTS

| 2007/0176109 A1 | 8/2007 | Bell |
| 2007/0223649 A1 | 9/2007 | De Godzinsky |
| 2010/0141820 A1 | 6/2010 | Chenebaux et al. |
| 2011/0013746 A1 | 1/2011 | Zeller et al. |

FOREIGN PATENT DOCUMENTS

| FR | 2943179 A1 | 9/2010 |
| WO | 2011008421 A1 | 1/2011 |

RADIATION SENSOR WITH X-RAY DETECTION

FIELD

The invention relates to medical imaging and, more specifically, to intraoral dental radiology. Modern dental radiology systems use image sensors employing silicon-based MOS technology, covered with a layer of scintillator material that converts X-rays to visible light within a wavelength spectrum to which silicon is sensitive. The image sensor integrates electric charges produced by the light which is itself produced by the scintillator.

BACKGROUND

The sensor comprises a matrix of active pixels, each pixel including a photosensitive element (most commonly a photodiode) and a number of transistors allowing the charges generated by light in the pixel to be collected in order to be converted to voltage. The sensor assembly is operated by a sequencing circuit in order to ensure that the pixels are reset and that the charges are integrated over a certain duration, starting from an instant in time of the start of integration, and lastly that the voltages representing the electric charges accumulated in the pixels are read out. These voltages are read out by a readout circuit placed at the base of each of the columns of pixels of the matrix. A row of pixels is read out by simultaneously addressing all of the pixels of this row using a row decoder; to achieve this, the pixels each comprise a row selection transistor which is turned on by a command from the row decoder, this being carried out simultaneously for all of the pixels of one and the same row. The row selection transistor then connects the pixel to a respective column conductor, common to all of the pixels of the same column of pixels, in order to transfer, to this column conductor, a useful signal representing the charges generated in the pixel located at the intersection of the selected row and the column in question. The transfer occurs simultaneously for all of the pixels of the row, each to its respective column conductor.

The radiological sensor is placed behind the human body part to be observed: for an intraoral dental radiological sensor, it is therefore placed inside the mouth of the patient, in proximity to the dental region to be observed. An X-ray source is placed outside the mouth of the patient, facing the sensor, and exposes the latter with a brief flash of X-rays through the biological tissues or other matter to be observed.

Among the significant constraints on the use of such a system, the risk of exposure of the patient and those around him or her to X-rays should be considered in particular. It is necessary to minimize the delivered dose of X-rays while still obtaining a good image of the observed region. It is for this reason that the X-ray source emits a brief flash corresponding to a limited dose of radiation.

This requires that the sensor is ready to record an image as soon as the flash is emitted, otherwise a portion of the delivered dose is wasted. However, it is also important that imaging does not start before the start of illumination, since even in the absence of X-rays the pixels collect electric charges due to the presence of dark currents in the photodiodes, i.e. currents produced even in the absence of light and hence in the absence of X-rays. These charges must be removed before the start of imaging.

An attempt is therefore made to synchronize the start of integration of useful charges in the photodiodes with the start of the X-ray flash. Similarly, an attempt is made to synchronize the end of integration of useful charges with the end of the X-ray flash.

In the prior art, multiple solutions have been used in order to achieve this synchronization.

One solution consists in using a wired connection between the sensor and the X-ray source in order to trigger the integration of an electronic image at the same time as the X-ray source is started up. It is however preferable to avoid a wired connection in the crowded medical environment in which the radiological image is taken. Furthermore, the wired connection requires a common protocol between the sensor and source, which is difficult to reconcile with the requirement for the sensor to be able to be exposed by any source, or, conversely, for the source to be able to illuminate any sensor.

It is therefore also proposed to place an X-ray detector beside the image sensor, inside the mouth or outside the mouth; this requires an additional component and a link between this component and the sensor.

In one particular situation that exclusively applies to a sensor using CCD technology and not to a sensor using MOS technology, the sensor having a CCD central charge transfer register to which the charges produced by the two halves of a sensor are transferred before being shifted stepwise towards a charge-to-voltage conversion circuit outside the matrix, it has previously been proposed (patent U.S. Pat. No. 5,510,623) not to mask the central register from light, whereas in fact it should be. The register is based on silicon and is therefore naturally photosensitive. It collects charges if it receives light and it transfers its charges stepwise to the charge-to-voltage conversion circuit. The resulting voltage level is continuously monitored; it represents dark current noise before the start of an X-ray flash; if this level increases substantially, it means that an X-ray flash has started and a complete image capture operation may be triggered. This solution is not transferable to CMOS sensors which do not have a readout charge transfer register; moreover, it interferes with the operation of the sensor by making the central register sensitive to light while it reads out the charges produced in the matrix, which negatively affects the image.

In yet another solution, using CCD technology, three X-ray detection diodes are placed behind the matrix of pixels. The resulting technology requires more manufacturing steps.

In another solution, pixels distributed throughout the matrix are used as reference pixels and are monitored in order to trigger the capture of an image if the level of a certain number of these reference pixels exceeds a threshold. This requires specific addressing means for reading out the reference pixels. This is also the case if reference zones of multiple pixels are used to carry out this detection.

In another solution, a detection cell which is larger than a pixel and capable of surrounding the entire matrix is provided for the purpose of detecting the arrival of an X-ray flash. This solution takes up space and detection potentially occurs where few X-rays arrive due to the obstacles through which they must pass.

In one particular solution, the overall image read out by the pixels is compared with an image taken in the dark before exposure to X-rays. When the read-out image suddenly becomes substantially different from the image taken in the dark, it is concluded that the flash has started. This requires that the entire matrix be read out in order to acquire this information on a sudden change in the luminosity level of the overall image.

Patent publication US 2007/0176109 recalls these various solutions, which are taken from various patent publications, and it proposes another solution using pixels for detecting the arrival of X-rays which have a quicker response time than the ordinary pixels of the matrix. These pixels are located on the periphery of the matrix and can be addressed by the same addressing means as the pixels of the matrix. They are preferably larger, and hence take up more space, than the pixels of the matrix.

In publication WO2011/008421, the matrix of pixels is read out using sub-sampling, i.e. not all of the pixels are read out; only those rows of pixels located on the periphery are actually read out in order to detect the arrival of X-rays. This complicates the internal arrangement of the sensor and its sequencing circuits.

In patent EP0757474, it is specified that the detection threshold is progressive and depends on the preceding image, in order to account for the fact that the dark current of the pixels which detect the arrival of the X-ray flash depends on the ambient temperature conditions, which can vary substantially.

In order to avoid the drawbacks of the devices of the prior art and at least to strike a better compromise between the constraints imposed by each of these devices, the invention proposes modifying the detection means present on the sensor.

An intraoral radiological image sensor using MOS technology is proposed, constructed in the following manner: it comprises a matrix of rows and columns of photosensitive pixels each comprising a photodiode and a circuit with transistors allowing the charges generated by light in the pixel to be collected and converted to voltage, with, for each column of pixels, a column conductor common to all of the pixels of the column, the column conductor being connected to a respective readout circuit for the column, and with a row-addressing circuit for addressing the pixels of a selected row and transferring, to the column conductors, useful signals arising from the pixels of the selected row and representing the illumination of these pixels.

The sensor according to the invention is characterized in that it includes, in the middle of the matrix and in place of a central column or a central row of pixels, a series of photodiodes which are all electrically connected in parallel on one side to a reference potential and on the other side to one and the same detection conductor extending along the series of photodiodes, this detection conductor being connected to a detection circuit delivering a signal for triggering the capture of an image when the detected current or the variation in this current exceeds a threshold showing that an X-ray flash has been initiated.

If the sensor is generally rectangular in shape (optionally with cut-off corners), therefore having a length and a width where the length is greater than the width, provision is made for the series of photodiodes to be positioned in place of a column or row oriented in the lengthwise direction. In most cases it is the columns (in the direction of signal collection) that are oriented in the lengthwise direction, but this is not obligatory; the series of photodiodes used to detect an X-ray flash and the detection conductor then extend in the direction of the column conductors which collect the useful signals.

The photodiodes are preferably distributed with the same spacing as the pixels in the columns or rows of pixels that surround it. These photodiodes are preferably technologically identical to the photodiodes of the pixels and they preferably have the same dimensions.

In particular embodiments, provision is also made for one or more other series of photodiodes, in columns, in rows or both, each occupying all or part of the column or row of pixels that they replace.

BRIEF DESCRIPTION OF THE DRAWINGS

Other features and advantages of the invention will become apparent upon reading the detailed description which follows, provided with reference to the appended drawings in which.

DETAILED DESCRIPTION

Figure 1:
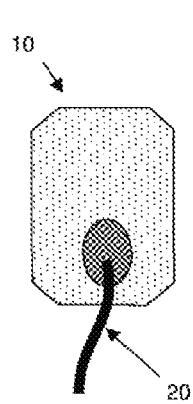
FIG. 1 shows a general view of a dental radiological sensor of the prior art.

FIG. 1 shows, at scale 1, an intraoral dental radiological sensor 10 comprising a visible image sensor covered with a scintillator that emits visible light under the effect of X-rays, the overall assembly being enclosed within a package the dimensions of which (a few centimeters to a side, a few millimeters in thickness) allow it to be introduced into the mouth of the patient. The sensor includes an output cable 20 but wireless communication would also be possible between the sensor and a computer being used to receive the electronic image.

The visible image sensor is made of monocrystalline silicon, which is sensitive to the visible light emitted by the scintillator. It is made up of a matrix of photosensitive pixels and control and readout circuits, which are capable of triggering the acquisition of an electronic image and of extracting, from each pixel, a useful signal representing the illumination of this pixel.

Figure 2:
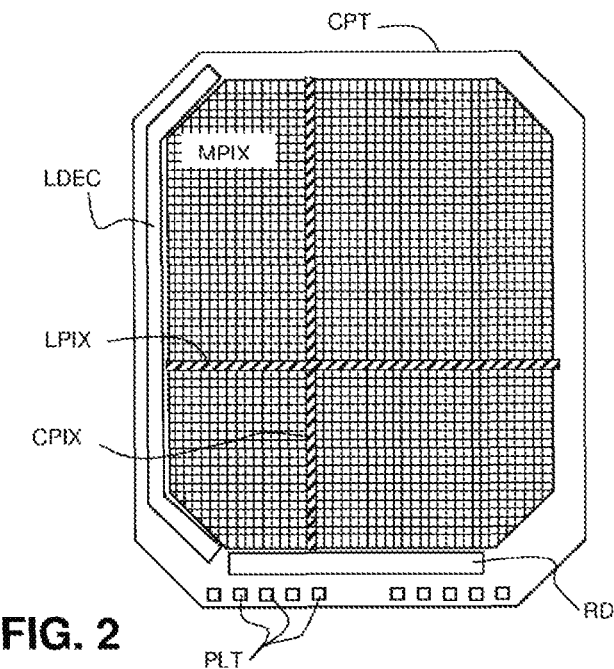
FIG. 2 shows the general arrangement of the matrix of pixels in one embodiment of the prior art.

For reasons of patient comfort, the package of the sensor may be rectangular in shape with cut-off corners as shown in FIG. 1, and the integrated circuit chip on which the matrix of pixels and the control and readout circuits are formed is itself preferably rectangular in shape with cut-off corners. Such an integrated circuit chip is shown in FIG. 2 and is denoted by the reference CPT. The matrix of photosensitive pixels is denoted by MPIX; it consists of a regular arrangement, with constant spacing, of columns of pixels and rows of pixels. The reference CPIX denotes a column of pixels taken by way of example and shown hatched; similarly, the reference LPIX denotes a row of pixels, taken by way of example and also shown hatched. The sequencing circuits, which comprise control and readout circuits, are symbolically represented here in a highly simplified manner by:

a row decoder LDEC, on one lengthwise lateral edge of the chip or even on both edges, which is used to address the various rows of pixels in succession by virtue of row conductors which each connect all of the pixels of one and the same row;

and a readout circuit RD which is used to extract the useful signal from the pixels of an addressed row; this signal is collected by column conductors which connect all of the pixels of one and the same column of pixels and it is guided by these conductors toward the readout circuit RD placed at the base of the matrix.

Output pads PLT of the integrated circuit chip allow analog or digital electronic signals representing the electronic image resulting from the exposure to X-rays to be sent out of the chip.

Hereinafter, since the terms "rows" and "columns" are terms which may be arbitrary, by convention, the word "row" will be considered to apply to rows of pixels extending in the direction of the row conductors addressed by the row decoder, and the word "column" will be considered to apply to columns of pixels extending in the direction of the column conductors which collect the useful signals from the pixels. Stated otherwise, the pixels are addressed row by row and the useful signal is collected at the base of the various columns.

When the sensor is rectangular (optionally with cut-off corners), rather than square (which is often the case), in shape, the columns are generally oriented in the lengthwise direction while the rows are oriented in the widthwise direction, but this is not obligatory.

Figure 3:
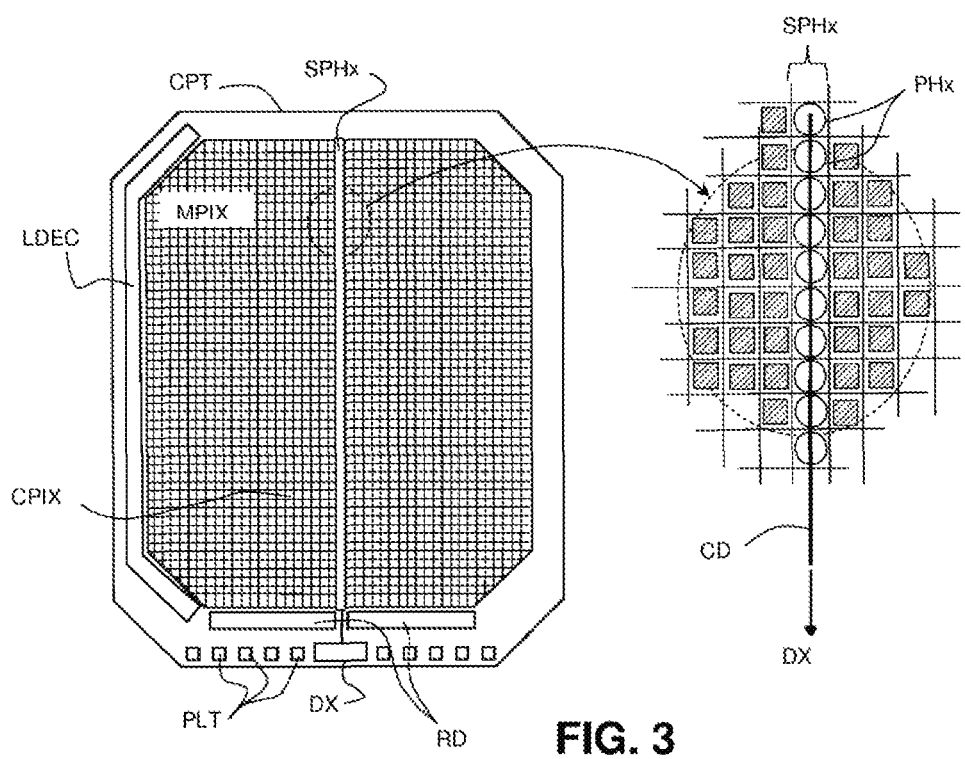
FIG. 3 shows the general arrangement of the matrix of pixels in a dental radiological sensor according to the invention.

FIG. 3 shows the arrangement of a sensor according to the invention. In the lengthwise direction of the sensor and in the middle of the matrix MPIX, one column of pixels has been replaced by a series SPHx of detection photodiodes, all of which are connected to one and the same detection conductor CD which extends along the replaced column and which is connected to a detection circuit DX located at the base of the matrix. FIG. 3 shows an enlarged local view that explains this better, in symbolic form: the matrix is composed of pixels distributed regularly with a certain spacing along the rows and each pixel is represented by a hatched square, each pixel comprising a photodiode and a number of transistors; one central column of the matrix is replaced by simple photodiodes, each represented by a circle, and these photodiodes are all directly connected to the common detection conductor CD, which is itself connected to the detection circuit DX. The spacing of the matrix is conserved, in the sense that the series of photodiodes occupies a maximum width that is equal to the row spacing of the pixels.

Preferably, the detection photodiodes of this series are distributed in the direction of the columns with the same column spacing as the pixels. The row and column spacings are in principle identical.

Again preferably and without being obligatory, the series of photodiodes extends over the entirety, or almost the entirety, of the height of the matrix of pixels.

Lastly, preferably, the photodiodes are identical in all respects (technology and dimensions) to the photodiodes which are present in the active pixels.

Figure 4:
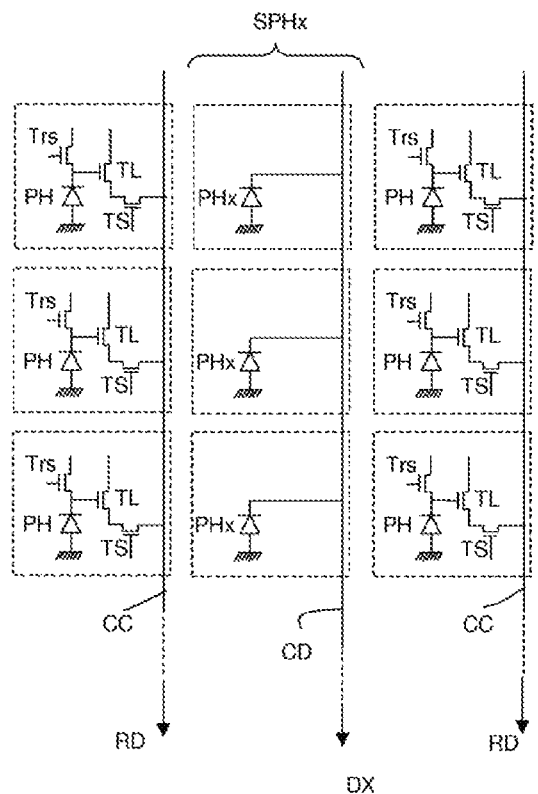
FIG. 4 shows a circuit diagram corresponding to the architecture of the sensor according to the invention.

FIG. 4 shows the circuit diagram corresponding to this arrangement, in an example in which each pixel comprises a photodiode PH and three MOS transistors, which are a transistor Trs for periodically resetting the photodiode at the start of integration, a readout transistor TL connected in a voltage follower configuration allowing the potential present on its gate to be copied to its source, and a row selection transistor TS controlled by a row conductor (not shown) connected to all of the transistors TS of one row controlled by the row decoder. The selection transistor connects, when it is turned on, the readout transistor to a column conductor CC. The sequencing circuits allowing an electronic image to be acquired at the moment of an X-ray flash (including the row decoder) are not shown in FIG. 4; they control the reset transistors and the row selection transistors. The pixel could include a fourth transistor or transfer transistor when the pixel is constructed with an intermediate storage node isolated from the photodiode by this transistor. The reset transistor is then used to reset the storage node. Lastly, a fifth transistor may be provided in order to reset the photodiode and the intermediate storage node separately.

The detection photodiodes of the series SPHx are each housed in the space reserved for a pixel but this space does not include any transistors (or, if it does include transistors for the purpose of simplifying the design patterns of the matrix, these transistors are not controlled like those of the pixels of the matrix and, in particular, they are not connected to the row decoder). These photodiodes PHx are all connected to ground, i.e. to a reference potential to which all of the photodiodes PH of the pixels are connected, and they are all additionally connected directly (i.e. without interposition of a controllable transistor) to the column conductor CD. The row decoder is therefore not used to address the photodiodes PHx, since these are systematically connected to the conductor CD and continuously provide the latter with the current that they generate under the effect of light in the presence of an X-ray flash or the inevitable dark current that they generate in the absence of X-rays.

The detection circuit DX has an input connected to the detection conductor CD. This circuit may have a very simple threshold comparison function and it delivers an output signal to the general sequencer of the matrix of pixels in order to authorize the triggering of a complete image capture operation when the current received by the detector exceeds a determined threshold.

The current threshold may be a fixed threshold or a threshold that is automatically adjusted according to environmental conditions (in particular according to temperature conditions). In the case of a fixed threshold, the threshold is chosen so as to have a value that is sufficient not to cause triggering under the effect of the dark current of the series of photodiodes when this current increases following a rise in temperature. In the case of an automatically adjusted threshold, multiple solutions may be envisaged. For example, provision may be made for a variable threshold that is generated by a temperature-sensitive circuit, the threshold increasing with temperature. Another possibility is for the threshold to be defined at a certain value above a mean of the dark current received on the conductor before exposure to X-rays; thus, only a sudden spike in current, due to an X-ray flash, would lead to the threshold being exceeded and trigger the capture of an image. Yet another possibility is for the threshold to be defined by a differential between two successive instants in time, the threshold being a growth gradient threshold of the received current.

In practice, the current is converted to voltage by a simple current-to-voltage conversion circuit, such as a capacitive transimpedance amplifier (CTIA), and it is this voltage which is used, as an absolute value or variation, in order to generate the signal authorizing the capture of an electronic image. A simple threshold voltage comparator will be used in the simplest case.

The series of detection photodiodes PHx placed in the middle of the matrix and in the longest, lengthwise direction of the rectangular sensor has the very substantial advantage of generally receiving a larger dose of X-rays (i.e. of light generated by the X-rays, but for the sake of simplicity and convenience a dose of X-rays will be spoken of) than photodiodes that are placed at the side of the matrix of pixels. Specifically, when the sensor is in the mouth, it is placed such that its medial row in the lengthwise direction is masked very little by the teeth or the jaw of the patient. Conversely, if one series of photodiodes is placed at the side of the matrix, it will often be masked by the jaw or the teeth and will receive many fewer X-rays. However, it is important that integration is triggered as soon as the X-ray flash starts to be received and it is therefore important that the series of photodiodes is masked as little as possible in order to react more quickly. The invention makes it possible to optimize the probability of rapid detection of the occurrence of the X-ray flash.

For example, when the desired image is an image taken with the mouth almost closed while the patient bites down on a sensor support, the sensor is placed on the support such that the medial row in the lengthwise direction is positioned along the support. Since the support is transparent to X-rays, it allows a dose of X-rays to pass directly onto the series of photodiodes aligned along the medial row of the sensor. Consequently, even in this particular case of the mouth being closed, the series of photodiodes is particularly well exposed to the X-rays.

Since the series of photodiodes occupies only the width of one column of pixels, it interferes only very little with the final electronic image. Typically, the pixels may be 20 micrometers by 20 micrometers in size, while the details of use to the practitioner for diagnostic purposes are rarely smaller than 100 micrometers by 100 micrometers in size. The luminance value of the missing pixel in each row is reconstructed by interpolation between the two neighbouring pixels of the same row, which is very easy to achieve since all of the missing pixels are located in the same medial position in the various rows.

The large number (many hundreds) of detection photodiodes PHx present in the series allows a sufficient detection current to be obtained without it being necessary for the detection photodiodes to have an area larger than one pixel.

The detection circuit DX will in principle be placed at the base of the matrix of pixels, with the readout circuits RD of the matrix. In FIG. 3 it is shown as being located below the readout circuits RD but this is not obligatory. Its placement depends in particular on its bulk, which is greater or lesser depending on the envisaged embodiment and depending on the desired functionalities (detection of occurrence of an X-ray flash, detection of received dose in order to stop image capture, triggering the end of the flash).

Manufacturing the series of photodiodes is very easy since the photodiodes are technologically identical to the photodiodes of the useful pixels of the matrix.

The series of detection photodiodes and the detection conductor CD may also be used to determine the end of image capture. Specifically, a signal representing the current received on the conductor CD may be integrated; the integral of the current then represents an X-ray dose received by the series of photodiodes. This dose is representative of the dose received by the patient. A circuit for controlling the end of integration may therefore be connected to the conductor CD like the circuit DX in order to detect the received dose and control the sequencing circuits in order to end the integration of electric charges in the pixels. The series of photodiodes and the detection conductor may be used to stop the X-ray flash once the received dose has reached a predetermined value. A circuit for controlling the end of the X-ray flash must then be connected to the detection conductor CD, and this circuit transmits a stop signal to the X-ray source (by wired connection for example) once the received dose is sufficient. The circuit for controlling the end of the X-ray flash may be the same as the circuit for controlling the end of integration.

In the case in which the rows of pixels decoded by the row decoder are oriented in the longest, lengthwise direction of the sensor, the series of photodiodes placed in the middle of the matrix in the longest, lengthwise direction replace one row of pixels by occupying the width of this row.

In order to ensure effective detection even in the case of the sensor being placed in the mouth such that the medial row of the sensor is partly masked by the jaw or the dentition, provision may be made for one or two other, secondary series of photodiodes aligned in the longest, lengthwise direction of the sensor in parallel to the first series and each replacing one respective column (or row) of pixels. These other series of photodiodes are all each connected to a conductor extending in parallel to the series and connected to the detection conductor CD. The currents of these other series are added to the current generated in the first series of photodiodes.

Figure 5:
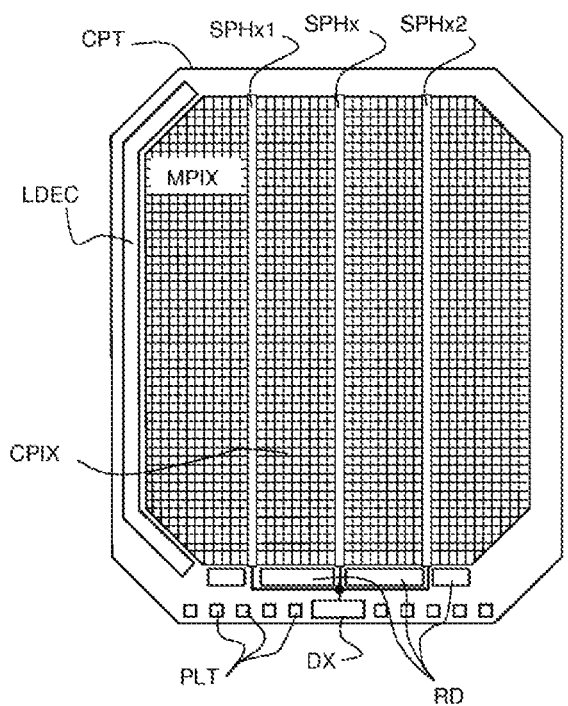
FIG. 5 shows an exemplary arrangement of the matrix with multiple series of detection photodiodes in columns.

FIG. 5 shows an example thereof with two other series of photodiodes SPHx1 and SPHx2 replacing two other columns of pixels, on either side of the central column SPHx, respectively. The image information is in this case also reconstructed by interpolation of the signals provided by two pixels located on a row on either side of a detection photodiode.

For this same purpose it is also possible to add a series of photodiodes aligned in a direction perpendicular to the length of the sensor. The common conductor which connects the photodiodes of this additional series is connected to the conductor CD of the first series SPHx such that the currents from the photodiodes of the two series are added together.

Figure 6:
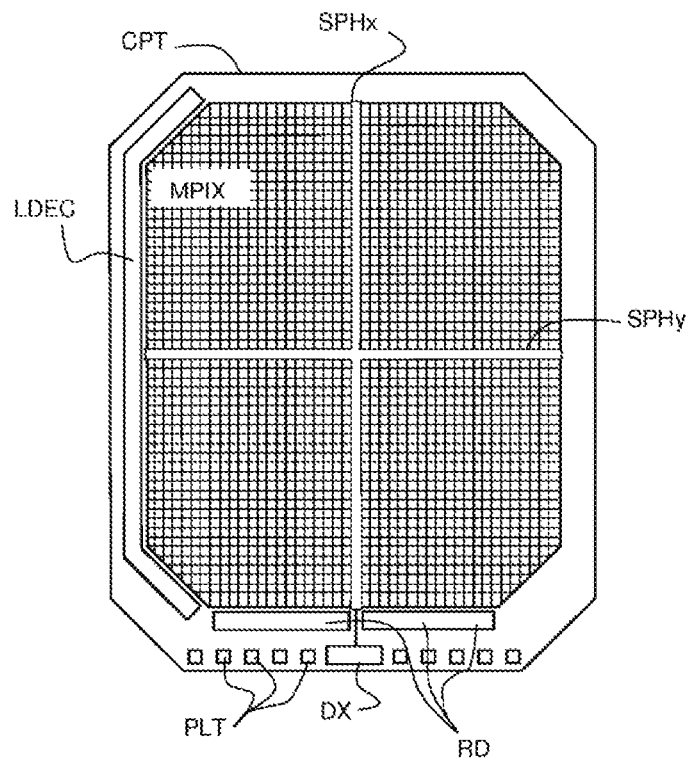
FIG. 6 shows an exemplary arrangement with one column and one row of detection photodiodes.

FIG. 6 shows an example thereof with a main series SPHx and a perpendicular secondary series SPHy. In this example, the secondary series is placed on a medial row of the matrix, but it could also be placed to one side or the other of this row; it is also possible to have two or three secondary series of photodiodes aligned in this direction. Again in this case, for each secondary series, the luminance received by a missing pixel is reconstructed by interpolation, but this time by interpolating the signals from two pixels placed in columns on either side of a given photodiode. This solution may be combined with that of FIG. 5 in which there are multiple series in columns in the lengthwise direction of the sensor. In any case, the conductors of all of the series are connected directly to the conductor CD of the central main series SPHx which is oriented in the longest, lengthwise direction.

Figure 7:
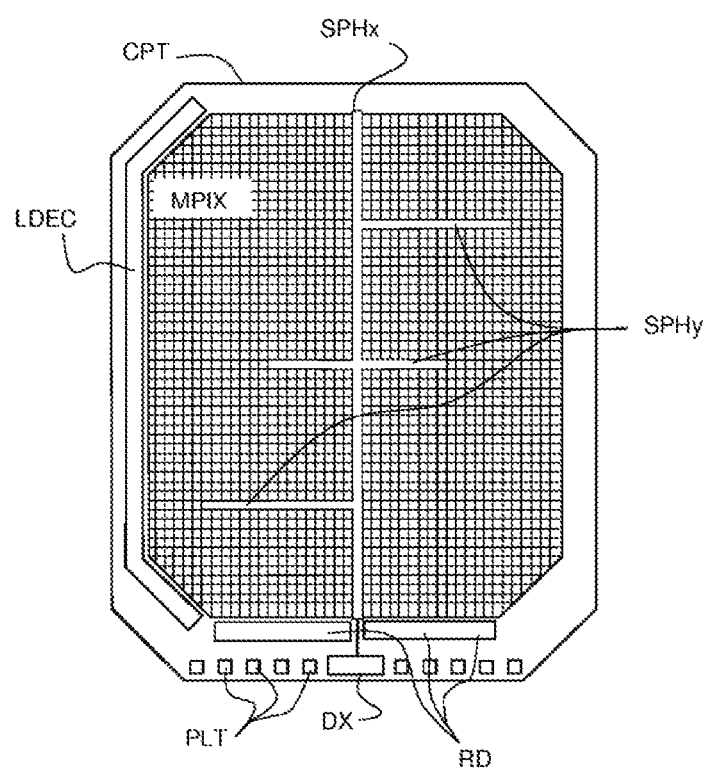
FIG. 7 shows an exemplary arrangement with a series of central photodiodes in a column and series of photodiodes in three different rows, each occupying only a portion of a row.

Lastly, FIG. 7 shows that the series of photodiodes do not necessarily extend over the entire length or the entire width of the matrix of pixels. FIG. 7 shows a central main series SPHx in a column, extending over the entire height of the matrix in the longest, lengthwise direction, and multiple series SPHy extending in the direction of the width, each over a portion of the width. The series preferably branch off the central series in order to facilitate the connection between the various conductors corresponding to each series, but this is not obligatory, the connection potentially also being made via the outside of the matrix.

The invention claimed is:

1. An intraoral radiological image sensor using MOS technology comprising a matrix of rows and columns of photosensitive pixels each comprising a photodiode and a circuit with transistors allowing the charges generated by light in the pixel to be collected and converted to voltage; and for each column of pixels, a column conductor common to all of the pixels of the column, the column conductor being connected to a respective readout circuit for the column;

a row-addressing circuit for addressing the pixels of a selected row and transferring, to the column conductors, useful signals arising from the pixels of the selected row and representing the illumination of these pixels; and the sensor including, in the middle of the matrix and in place of a central column or a central row of pixels, a series of detection photodiodes which are all electrically connected on one side to a reference potential and on the other side to one and the same detection conductor extending along the series of photodiodes, this detection conductor being connected to a detection circuit delivering a signal for triggering the capture of an image when the detected current or the variation in this current exceeds a threshold showing that an X-ray flash has been initiated.

2. The radiological image sensor of claim 1 being generally rectangular in shape, optionally with cut-off corners, and therefore having a length and a width where the length is greater than the width, wherein the series of detection photodiodes is positioned in place of a central column or row oriented in the lengthwise direction, the detection conductor extending in the lengthwise direction.

3. The radiological image sensor of claim 2, wherein the detection conductor extends in the direction of the column conductors.

4. The image sensor of claim 1, wherein the detection photodiodes are distributed with the same spacing as the pixels in the columns or rows of pixels that surround it.

5. The image sensor of claim 1, wherein the detection photodiodes are technologically identical to the photodiodes of the pixels and they preferably have the same dimensions.

6. The image sensor of claim 1, wherein it includes at least one other series of photodiodes which is parallel or perpendicular to the first series, all of the photodiodes of the other series being connected directly to a common conductor which is itself connected to the detection conductor.

7. The image sensor of claim 6, wherein one or more of the series of photodiodes occupies only a portion of the length of a row or of a column of pixels of the matrix.

* * * * *